(12) United States Patent
Solitario, Jr. et al.

(10) Patent No.: US 9,131,966 B2
(45) Date of Patent: Sep. 15, 2015

(54) VERTEBRAL MANIPULATION ASSEMBLY

(71) Applicant: DePuy Synthes Products, Inc., Raynham, MA (US)

(72) Inventors: Ralph C. Solitario, Jr., West Chester, PA (US); Eric Biester, Raynham, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 158 days.

(21) Appl. No.: 13/792,299

(22) Filed: Mar. 11, 2013

(65) Prior Publication Data

US 2014/0257312 A1   Sep. 11, 2014

(51) Int. Cl.
*A61B 17/88* (2006.01)
*A61B 17/70* (2006.01)
*A61B 17/02* (2006.01)

(52) U.S. Cl.
CPC ..... *A61B 17/7079* (2013.01); *A61B 2017/0256* (2013.01)

(58) Field of Classification Search
CPC . A61B 17/88; A61B 17/8866; A61B 17/7079
USPC .......................... 606/86 R, 90, 105, 246–279
See application file for complete search history.

(56) References Cited

U.S. PATENT DOCUMENTS

| 225,041 | A | 3/1880 | Barber |
|---|---|---|---|
| 237,347 | A | 2/1881 | Warner |
| 357,540 | A | 2/1887 | Seely |
| 495,749 | A | 4/1893 | Muron |
| 521,934 | A | 6/1894 | Lineback |
| 552,957 | A | 1/1896 | De Gonzalez |
| 567,666 | A | 9/1896 | Tallerday |
| 1,710,092 | A | 4/1929 | Hitchcock |

(Continued)

FOREIGN PATENT DOCUMENTS

| EP | 2 258 292 | 12/2010 |
|---|---|---|
| WO | WO 2005/009209 | 2/2005 |

(Continued)

OTHER PUBLICATIONS

U.S. Appl. No. 13/652,920, filed Oct. 16, 2012, Masson.

*Primary Examiner* — Christopher Beccia
(74) *Attorney, Agent, or Firm* — Baker & Hostetler LLP

(57) ABSTRACT

A vertebral manipulation assembly includes a vertebral fixation assembly that is configured to be attached to a first vertebra and a second vertebra that is spaced from the first vertebra. The vertebral fixation assembly can include vertebral fixation members that attach to the first and second vertebrae, respectively. The vertebral manipulation assembly can further include a vertebral manipulation instrument that is configured to be coupled to the vertebral fixation assembly, and provide a first compression force that biases the first and second vertebral fixation members to move toward each other, and a second distraction force that biases the first and second vertebral fixation members to move away from each other. The vertebral manipulation instrument can include a coarse adjustment assembly that, when actuated, causes the first and second vertebral fixation members to incrementally move with respect to each other in first increments. The vertebral manipulation instrument can further include a fine adjustment assembly that, when actuated, allows for finer adjustment of the position of the first and second vertebral fixation members.

21 Claims, 10 Drawing Sheets

(56) References Cited

U.S. PATENT DOCUMENTS

| | | |
|---|---|---|
| 2,333,033 A | 10/1943 | Mraz |
| 3,861,432 A | 1/1975 | Rothenberger |
| 4,733,657 A | 3/1988 | Kluger |
| 4,848,368 A | 7/1989 | Kronner |
| 6,451,019 B1 | 9/2002 | Zucherman et al. |
| 6,491,695 B1 * | 12/2002 | Roggenbuck ............... 606/86 A |
| 7,011,658 B2 | 3/2006 | Young |
| 7,578,822 B2 | 8/2009 | Rezach et al. |
| 7,776,051 B2 | 8/2010 | Colleran et al. |
| 7,811,288 B2 | 10/2010 | Jones et al. |
| 8,192,440 B2 | 6/2012 | Jones et al. |
| 8,197,488 B2 | 6/2012 | Sorrenti et al. |
| 2005/0021040 A1 | 1/2005 | Bertagnoli |
| 2005/0203532 A1 | 9/2005 | Ferguson et al. |
| 2008/0077155 A1 * | 3/2008 | Diederich et al. ............ 606/105 |
| 2008/0177270 A1 | 7/2008 | Sorrenti et al. |
| 2008/0255567 A1 | 10/2008 | Accordino |
| 2009/0209965 A1 | 8/2009 | Lewis |
| 2010/0024487 A1 | 2/2010 | Khoo et al. |
| 2010/0030283 A1 * | 2/2010 | King et al. .................. 606/86 A |
| 2010/0036443 A1 | 2/2010 | Hutton et al. |
| 2010/0274252 A1 | 10/2010 | Bottomley et al. |
| 2010/0314817 A1 | 12/2010 | Li et al. |
| 2010/0331849 A1 | 12/2010 | Riesinger et al. |
| 2014/0107656 A1 | 4/2014 | Masson et al. |

FOREIGN PATENT DOCUMENTS

| | | |
|---|---|---|
| WO | WO 2008/048450 | 4/2008 |
| WO | WO 2010/014296 | 2/2010 |
| WO | WO 2011/002847 | 1/2011 |

* cited by examiner

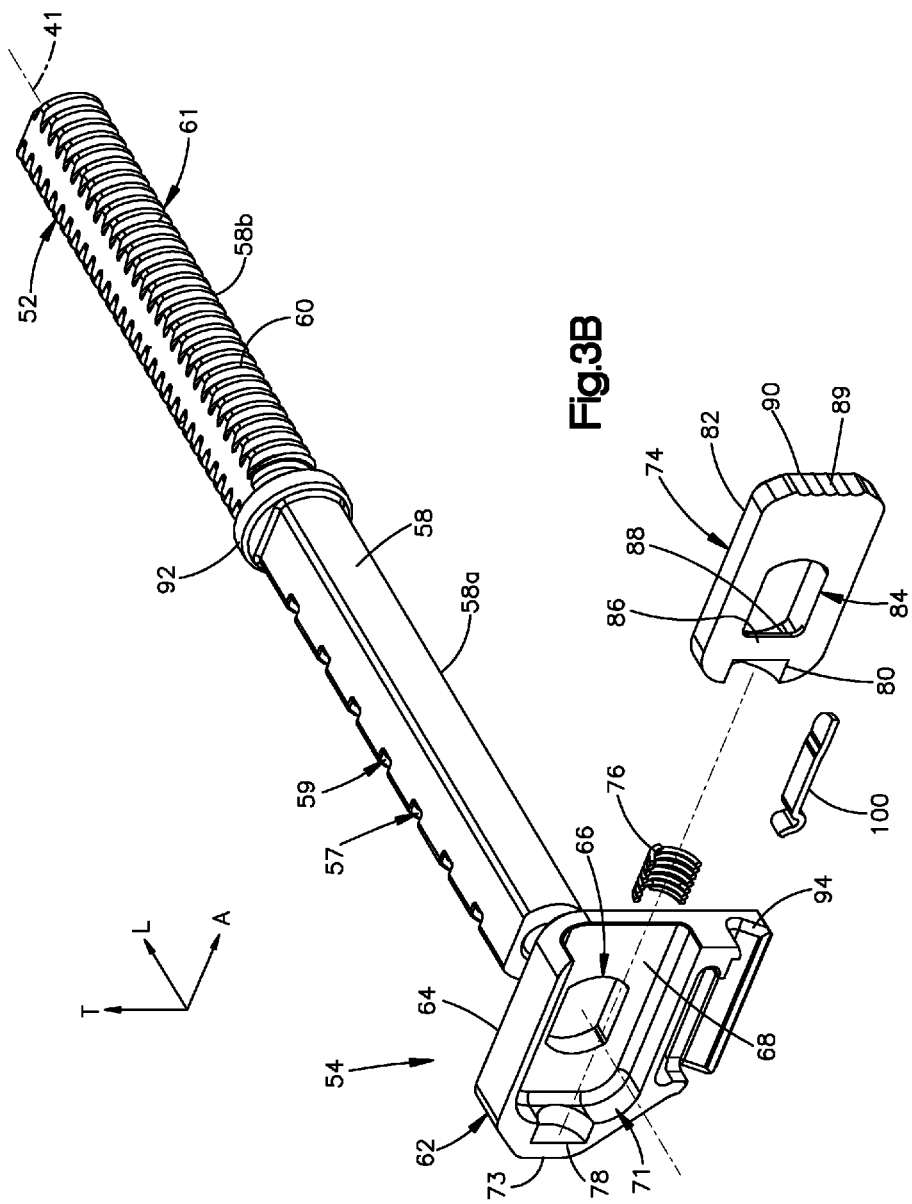

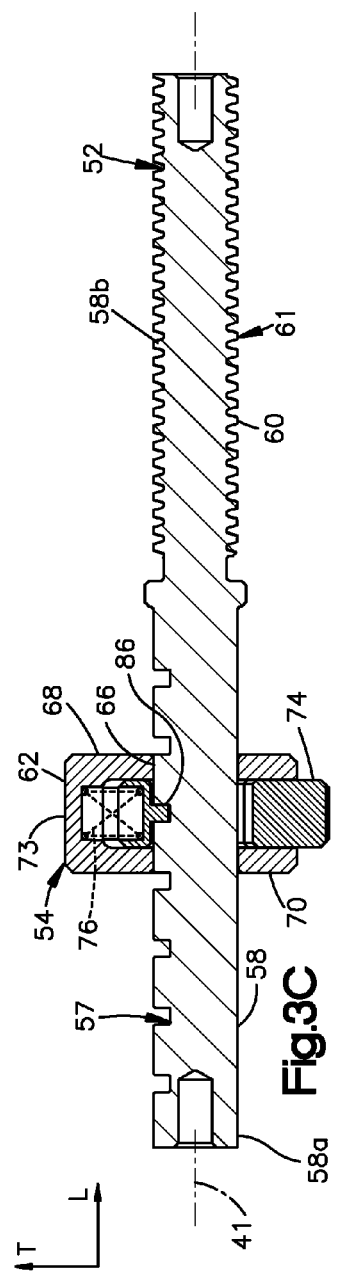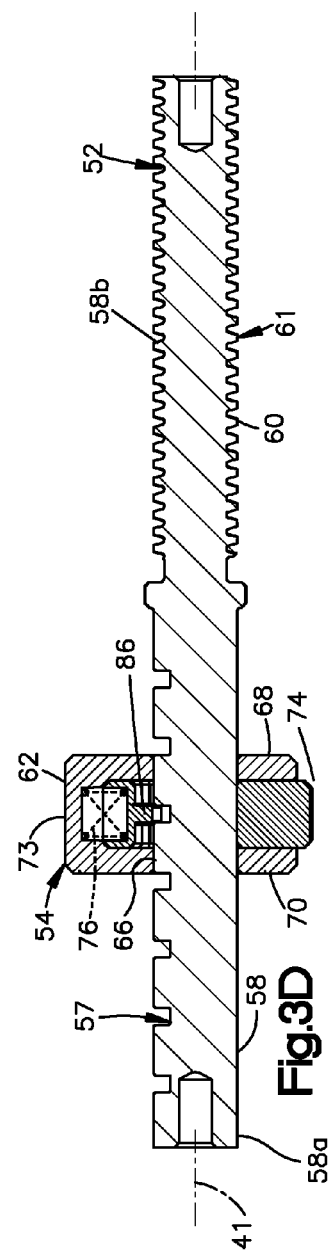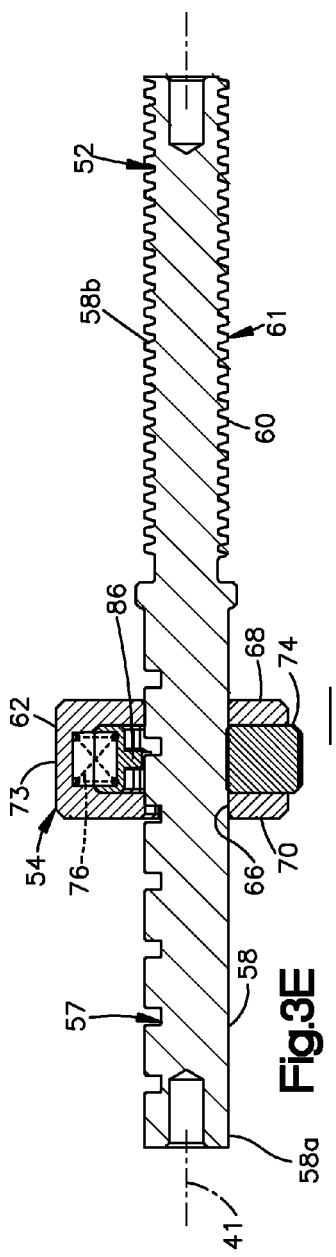

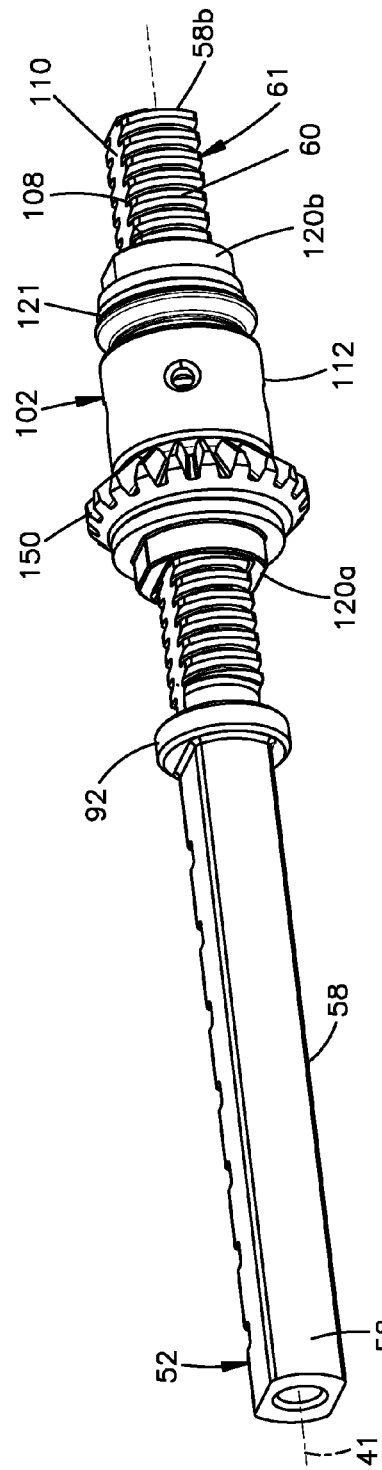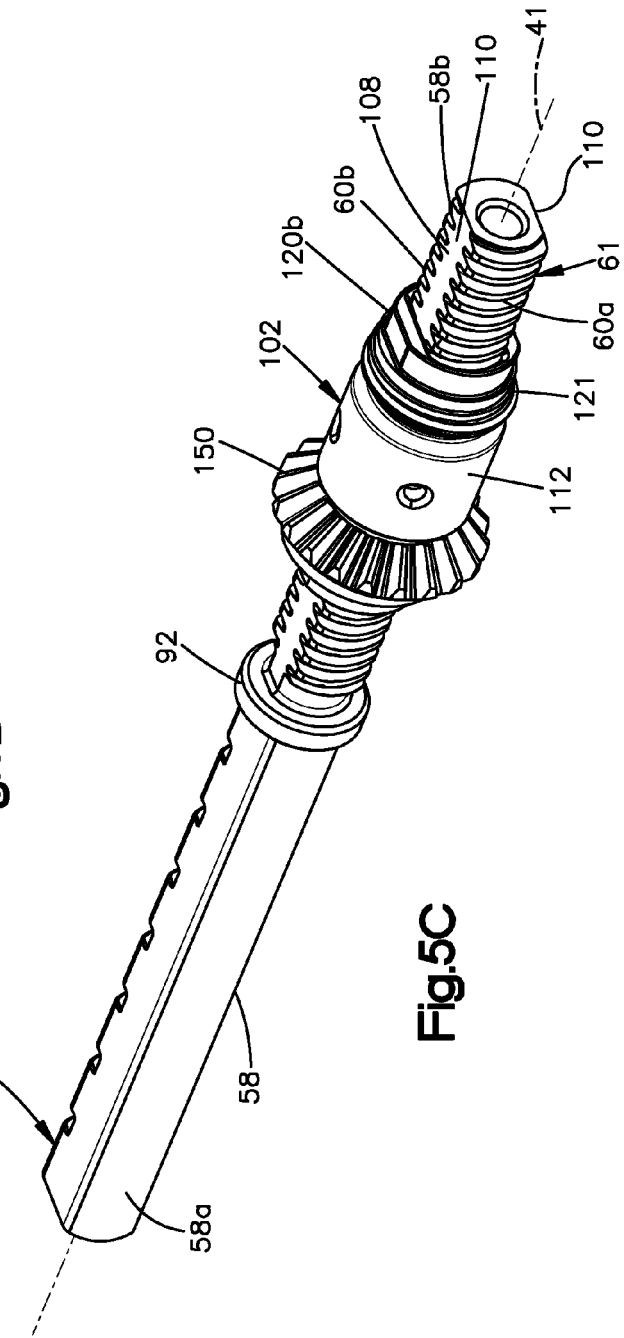
Fig.5B
Fig.5C

VERTEBRAL MANIPULATION ASSEMBLY

BACKGROUND

Spinal surgery often requires removal of the existing intervertebral disc tissue located between adjacent vertebrae and replacement thereof with an intervertebral implant which may take the form of a cage or other fusion device or implant which may be of the type which allows limited universal movement of the adjacent vertebrae with respect to each other.

It may be desired to initially separate the adjacent vertebrae from each other and to retain them apart, for instance prior to cleaning out the existing disc tissue and inserting the intervertebral implant. To distract adjacent vertebrae away from each other, an implant system includes an instrument and a pair of anchor screws, one anchored in each of the adjacent vertebrae. The instrument is configured to engage the screws so as to positionally adjust the vertebrae.

SUMMARY

In accordance with one embodiment, a vertebral manipulation instrument includes a connecting rod that is elongate along a longitudinal direction and defines a first plurality of adjustment locations and a second plurality of adjustment locations. The vertebral manipulation instrument can further include a first arm supported by the connecting rod, the first arm configured to engage a first bone fixation member, and a second arm supported by the connecting rod, the second arm configured to engage a second bone fixation member. The vertebral manipulation instrument can further include a coarse adjustment assembly that is configured to be actuated so as to move the first arm from a first one of the first plurality of adjustment locations to a second one of the first plurality of adjustment locations that is adjacent the first one of the first plurality of adjustment locations, and lock the first arm with respect to movement from the second one of the first plurality of adjustment locations. The first one of the first plurality of adjustment locations is spaced a first distance from the second one of the adjustment locations along the longitudinal direction. The vertebral manipulation instrument can further include a fine adjustment assembly that is configured to be actuated so as to move the second arm from a first one of the second plurality of adjustment locations to a second one of the second plurality of adjustment locations that is spaced a second distance from the first one of the second plurality of adjustment locations a second distance along the longitudinal direction. The second distance can be less than the first distance.

BRIEF DESCRIPTION OF THE DRAWINGS

The foregoing summary, as well as the following detailed description of illustrative embodiments of spreader system of the present application, will be better understood when read in conjunction with the appended drawings. For the purposes of illustrating the spreader system of the present application, there is shown in the drawings illustrative embodiments. It should be understood, however, that the application is not limited to the precise arrangements and instrumentalities shown. In the drawings:

FIG. 3B is another exploded perspective of the coarse adjustment assembly of the vertebral manipulation instrument illustrated in FIG. 3A, showing a portion of the coarse adjustment assembly in cross-section;

FIG. 3C is a sectional side elevation view of the coarse adjustment assembly illustrated in FIG. 3B, shown in a locked configuration;

FIG. 3D is a sectional side elevation view of the coarse adjustment assembly illustrated in FIG. 3C, show in an unlocked configuration;

FIG. 3E is a sectional side elevation view of the coarse adjustment assembly illustrated in FIG. 3C, show in an adjusted position;

FIG. 5B is a perspective view of the traveler assembly illustrated in FIG. 5A;

FIG. 5C is another perspective view of the traveler assembly illustrated in FIG. 5A.

DETAILED DESCRIPTION

Figure 1A:
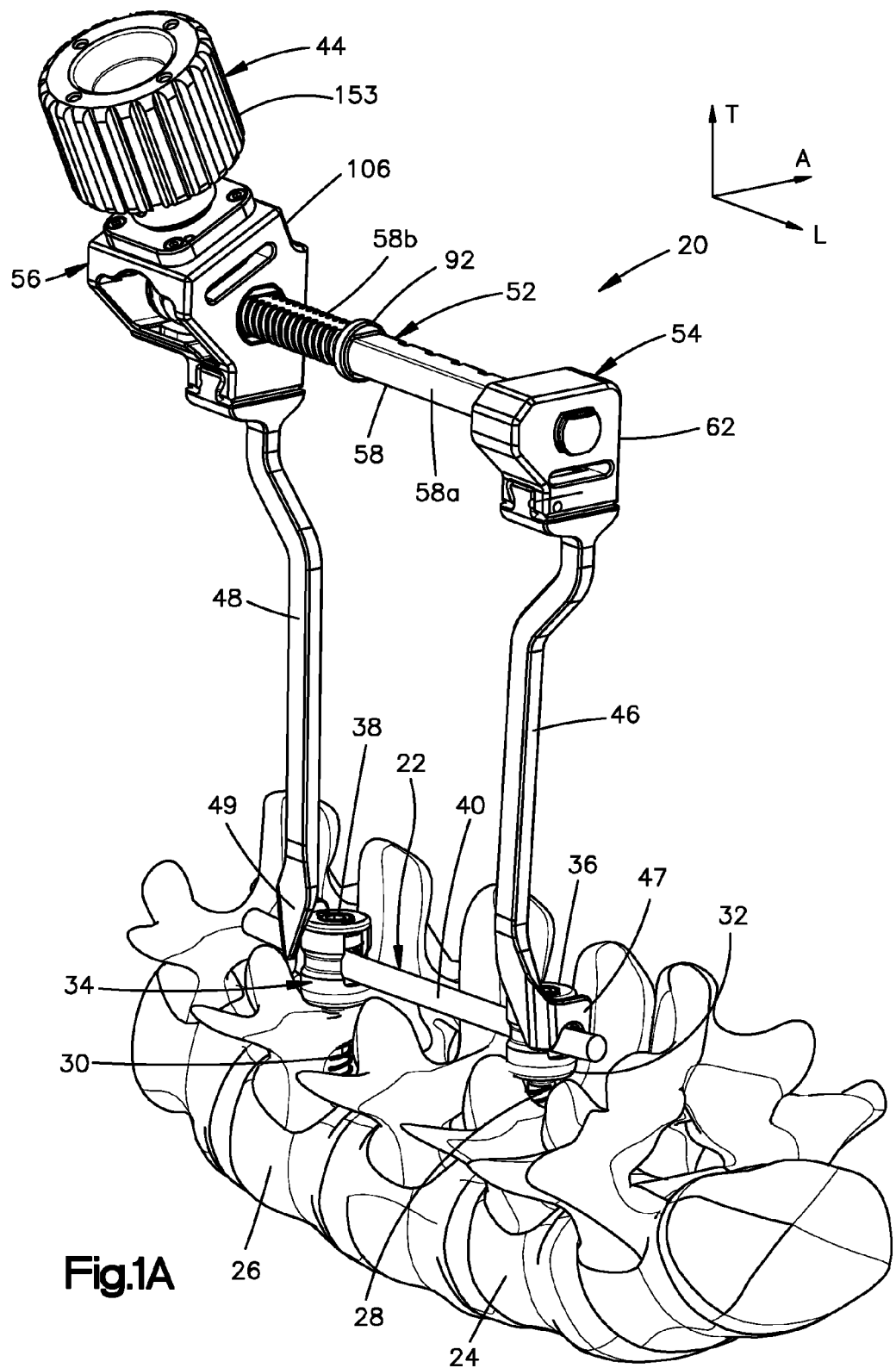
FIG. 1A is a perspective view of a vertebral manipulation assembly including a vertebral fixation assembly shown attached to first and second vertebrae, and a vertebral manipulation instrument coupled to the pedicle screw assembly, shown configured to compress the first and second vertebrae toward each other.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

Referring to FIG. 1A, a bone manipulation assembly, such as a vertebral manipulation assembly 20 includes a bone fixation assembly, such as a vertebral fixation assembly 22 shown attached to a first vertebra 24 and a second vertebra 26 that is spaced from the first vertebra. For instance, the first and second vertebrae 24 and 26 can be adjacent to each other, and separated by an intervertebral space, or one or more additional vertebrae can be disposed between the first and second vertebra 24 and 26. The bone fixation assembly can include a first bone anchor, such as a first vertebral bone anchor 28 that is configured to be fixed to a first bone such as the first vertebra 24, and a second bone anchor such as a second vertebral bone anchor 30 that is configured to be fixed to a second bone, such as the second vertebra 26. For instance, the vertebral bone anchors 28 and 30 can define pedicle screws that are threadedly inserted into the pedicle regions of the first and second vertebrae 24 and 26, respectively. Thus, the vertebral fixation assembly 22 can include at least first and second pedicle screw assemblies 32 and 34, respectively, that each includes the corresponding first and second vertebral bone anchors 28 and 30, corresponding first and second locking caps 36 and 38, respectively, that are configured to be affixed to the respective first and second bone anchors 28 and 30.

The vertebral fixation assembly 22 can further include a spinal fixation rod 40 that is configured to be retained by the first and second pedicle screw assemblies 32 and 34. For instance, the spinal fixation rod 40 is configured to be disposed between the first locking cap 36 and the first vertebral bone anchor 28, and is further configured to be disposed between the second locking cap 38 and the second vertebral bone anchor 30. When the first and second locking caps 36 and 38 are in an untightened state on the respective first and second bone anchors 28 and 30, the first and second pedicle screw assemblies 32 and 34 are translatable along the spinal fixation rod 40. When the respective first and second locking caps 36 and 38 are tightened, the first and second pedicle screw assemblies 32 and 34 are fixed with respect to translation along the spinal fixation rod 40.

The present disclosure recognizes that it may be desirable to move one or both of the first and second vertebrae 24 and 26 toward or away from the other of the first and second vertebrae 24 and 26. For instance, it may be desirable to distract one or both of the first and second vertebrae 24 and 26 away from the other of the first and second vertebrae 24 and 26, for instance when it is desired to access an intervertebral space disposed between the first and second vertebra 24 and 26, for example when inserting an implant into the intervertebral space or when performing a full or partial corpectomy. It may also be desirable to compress one or both of the first and second vertebrae 24 and 26 toward the other of the first and second vertebrae 24 and 26 so as to adjust the size of the intervertebral space.

Figure 2:
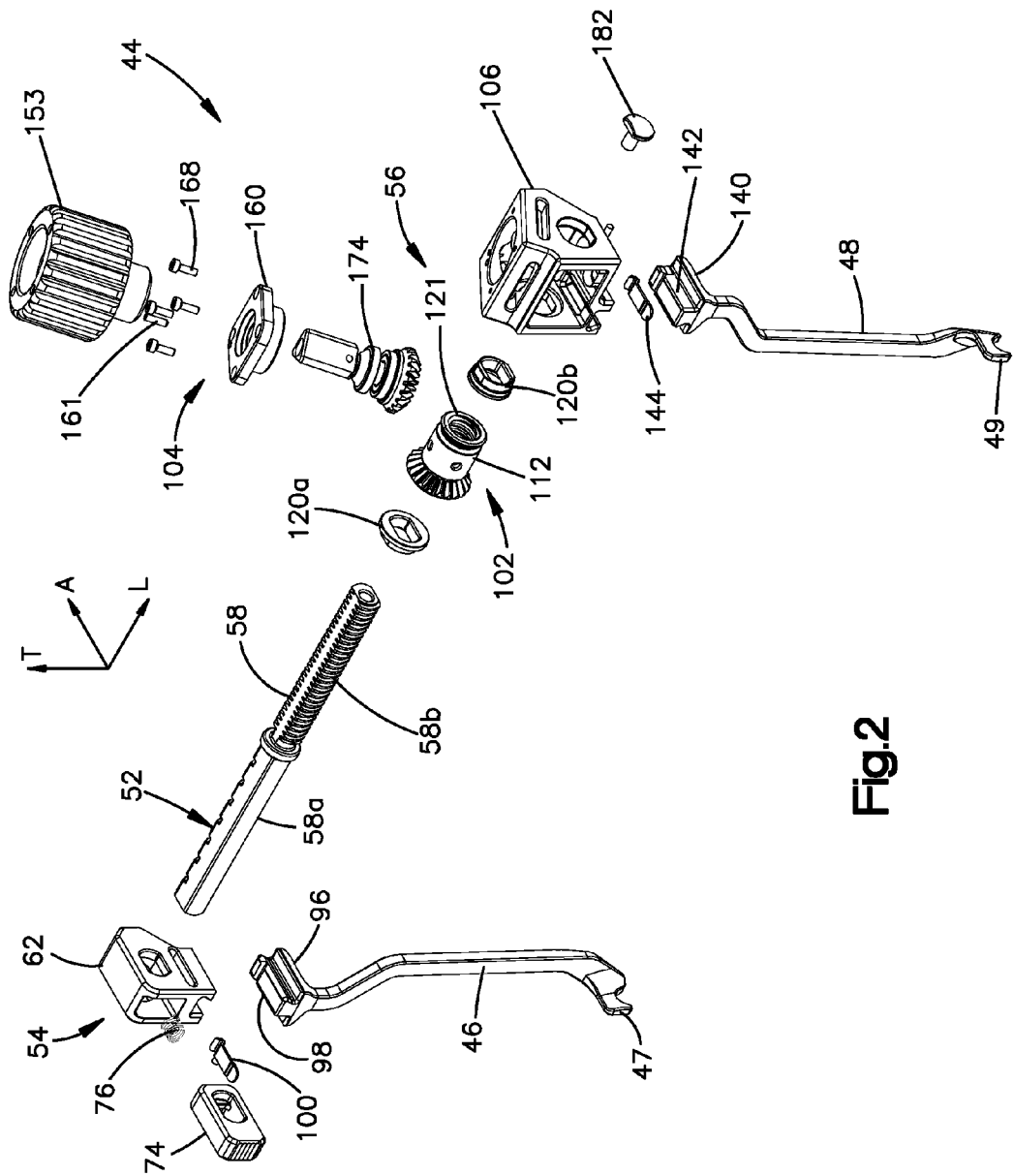
FIG. 2 is an exploded perspective view of the vertebral manipulation instrument illustrated in FIGS. 1A-B.

Accordingly, the vertebral manipulation assembly 20 can further include a bone manipulation instrument, such as a vertebral manipulation instrument 44 that is configured to be coupled to the vertebral fixation assembly 22, and to provide a first compression force that biases the first and second vertebral bone anchors 28 and 30 to move toward each other, and a second distraction force that biases the first and second vertebral bone anchors 28 and 30 to move away from each other. The vertebral manipulation instrument 44 can be made from any suitable biocompatible material, such as titanium, stainless steel, aluminum, alloys thereof, and plastic. As illustrated in FIG. 2, the vertebral manipulation instrument 44 can include a first arm 46, a second arm 48, and a connecting rod 52 that supports the first arm 46 and the second arm 48, and extends between the first arm 46 and the second arm 48, such that at least one of the first and second arms 46 and 48 is configured to move relative to the other, for instance toward and away from the other, along the connecting rod 52.

As will be described in more detail below, the vertebral manipulation instrument 44 can further include a first or coarse adjustment assembly 54 that couples the first arm 46 to the connecting rod and that, when actuated, causes at least one of the first and second arms 46 and 48 to move with respect to the other of the first and second arms 46 and 48 along the connecting rod 52 in first increments. For instance, the coarse adjustment assembly 54 can couple the first arm 46 to the connecting rod 52 as illustrated. The vertebral manipulation instrument 44 can further include a second or fine adjustment assembly 56 that couples the second arm 48 to the connecting rod 52 and that, when actuated, causes at least one of the first and second arms 46 and 48 to move with respect to the other of the first and second arms 46 and 48 along the connecting rod 52 in second increments that are less than the first increments. For instance, the second increments can be continuous and not defined at discrete locations.

Referring again to FIG. 1A, the first and second arms 46 and 48 can define distal engagement ends 47 and 49, respectively, that are configured to engage the first and second vertebral fixation anchors 28 and 30, respectively, for instance directly or indirectly via the first and second locking caps 36 and 38, respectively. For instance, the distal engagement ends 47 and 49 can define paddles having substantially curved ends that are thus sized and shaped to abut or otherwise engage the spinal fixation rod 40 such that the first and second vertebral bone anchors 28 and 30 are disposed between the first and second arms 46 and 48. The first and second arms 46 and 48, for instance at the distal engagement ends 47 and 49, can bear, directly or indirectly, against the first and second vertebral bone anchors 28 and 30, respectively. For instance, the paddles defined at the distal engagement ends 47 and 49 can bear against the first and second vertebral bone anchors 28 and 30, respectively. Thus, as the first and second arms 46 and 48 are biased to move toward each other the first and second arms 46 and 48 apply a compressive force to the first and second vertebral bone anchors 28 and 30 that biases the first and second vertebral bone anchors 28 and 30 to move toward each other.

The biasing compression force of the first and second arms 46 and 48 causes each of the first and second vertebral bone anchors 28 and 30 to travel toward the other of the first and second vertebral bone anchors 28 and 30 along the spinal fixation rod 40 when the respective first and second locking caps 36 and 38 are in their respective untightened states. It is envisioned that one of the first and second locking caps 36 and 38 can be in the untightened state while the other of the first and second locking caps 36 and 38 is in the tightened state, such that only one of the first and second vertebral bone anchors 28 and 30 moves with respect to the other of the first and second vertebral bone anchors 28 and 30. Thus, it can be said that the biasing compression force of the first and second arms 46 and 48 causes at least one of the first and second vertebral bone anchors 28 and 30 to move toward the other, via the biasing compression force applied to the first and second vertebral bone anchors 28 and 30, respectively. For instance, the biasing compression force applied directly to the first and second vertebral bone anchors 28 and 30, respectively, or indirectly via the biasing force that is applied to the first and second locking caps 36 and 38, respectively, and then communicated to the first and second vertebral bone anchors 28 and 30, respectively. When the first and second vertebral bone anchors 28 and 30 are attached to the respective first and second vertebrae 24 and 26, the biasing compression force causes at least one of the respective first and second vertebrae 24 and 26 to move toward the other of the first and second vertebrae 24 and 26.

Figure 1B:
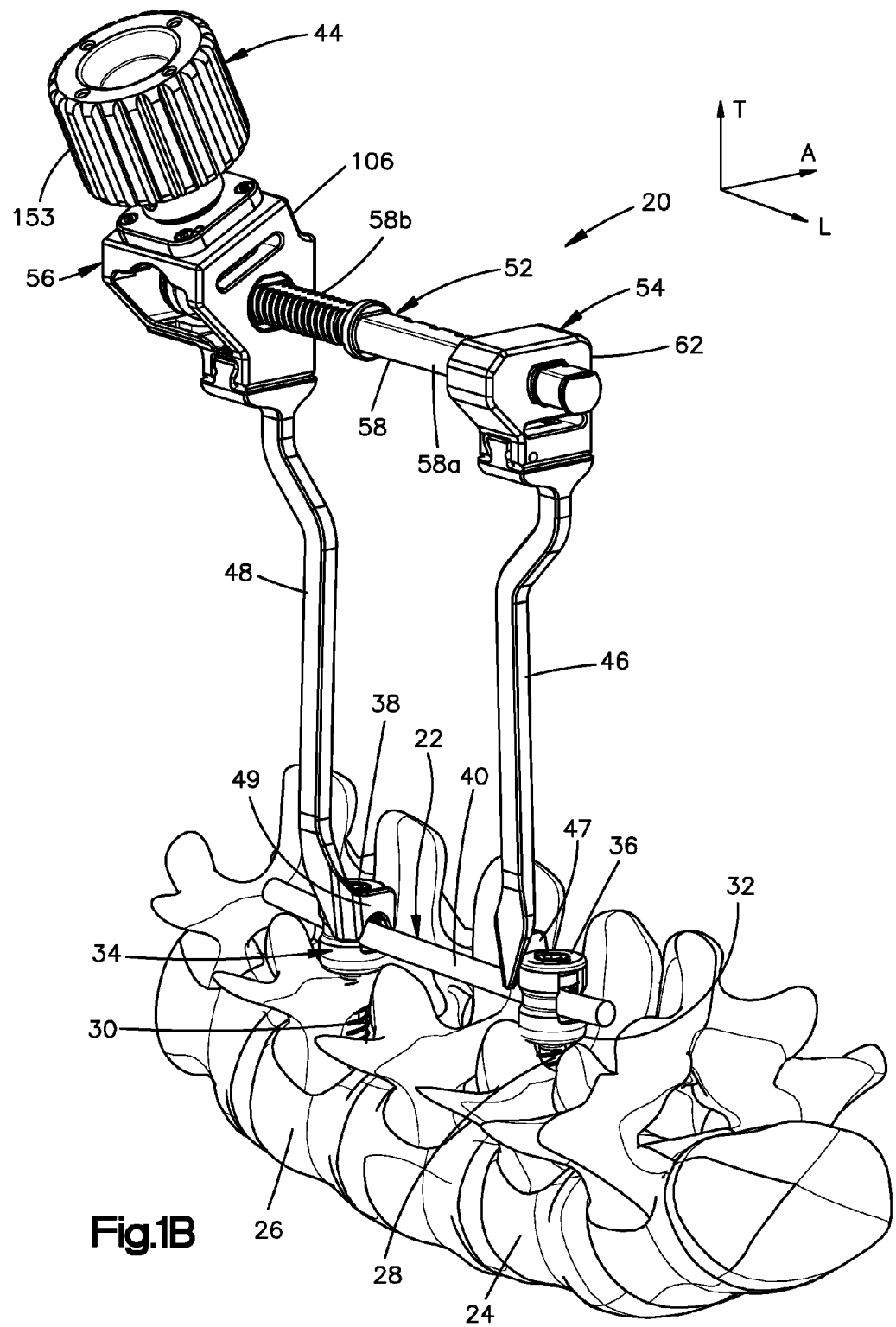
FIG. 1B is a perspective view of the vertebral attachment assembly illustrated in FIG. 1A, showing the vertebral manipulation instrument coupled to the pedicle screw assembly, shown configured to distract the first and second vertebrae away from each other.

Referring to FIG. 1B, the first and second arms 46 and 48 can abut or otherwise engage the spinal fixation rod 40 such that the first and second arms 46 and 48 are disposed between the first and second vertebral bone anchors 28 and 30, and the first and second arms 46 and 48 bear, directly or indirectly, against the first and second vertebral bone anchors 28 and 30, respectively. Thus, as the first and second arms 46 and 48 are biased to move away from each other, the first and second arms 46 and 48 apply a distraction force to the first and second vertebral bone anchors 28 and 30 that biases the first and second vertebral bone anchors 28 and 30 to move away each other.

The biasing distraction force of the first and second arms 46 and 48 causes each of the first and second vertebral bone anchors 28 and 30 to travel away from the other of the first and second vertebral bone anchors 28 and 30 along the spinal fixation rod 40 when the respective first and second locking caps 36 and 38 are in their respective untightened states. It is envisioned that one of the first and second locking caps 36 and 38 can be in the untightened state while the other of the first and second locking caps 36 and 38 is in the tightened state, such that only one of the first and second vertebral bone anchors 28 and 30 moves with respect to the other of the first and second vertebral bone anchors 28 and 30. Thus, it can be said that the biasing distraction force of the first and second arms 46 and 48 causes at least one of the first and second vertebral bone anchors 28 and 30 to move away from the other. When the first and second vertebral bone anchors 28 and 30 are attached to the respective first and second vertebrae 24 and 26, the biasing distraction force causes at least one of the respective first and second vertebrae 24 and 26 to move away from the other of the first and second vertebrae 24 and 26.

It should be appreciated that while the vertebral fixation assembly 22 has been described in accordance with one embodiment, the vertebral fixation assembly 22 can be alternatively constructed as desired. Furthermore, it should be appreciated that the first and second arms 46 and 48 can attach to the vertebral fixation assembly 22 in any alternative manner as desired. For instance, the first and second arms 46 and 48 can attach to the first and second vertebral bone anchors 28 and 30 as described in U.S. Patent Publication No. 2005/0021040 and U.S. patent application Ser. No. 13/652,920, the disclosure of each of which is incorporated by reference as if set forth in its entirety herein. During operation, the coarse adjustment assembly 54 can be actuated to bring the first and second arms 46 and 48 into relative proximity with the first and second vertebral bone anchors 28 and 30, respectively, and the fine adjustment assembly 56 can cause the first and second arms 46 and 48 to bear against the first and second vertebral bone anchors 28 and 30, respectively. Further adjustment of the fine adjustment assembly 56 can cause the first and second arms 46 and 48 to apply the compressive or distractive biasing forces as described above.

Referring now to FIG. 2, the vertebral manipulation instrument 44 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the vertebral manipulation instrument 44 is coupled to the first and second vertebrae 24 and 26, the transverse direction T may extend vertically generally along the anterior-posterior direction, while the horizontal plane defined by the longitudinal direction L and lateral direction A lies generally in the anatomical plane defined caudal-cranial direction and the medial-lateral direction, respectively. Accordingly, the directional terms "vertical" and "horizontal" are used to describe the vertebral manipulation assembly 20 and its components as illustrated merely for the purposes of clarity and illustration.

Figure 3A:
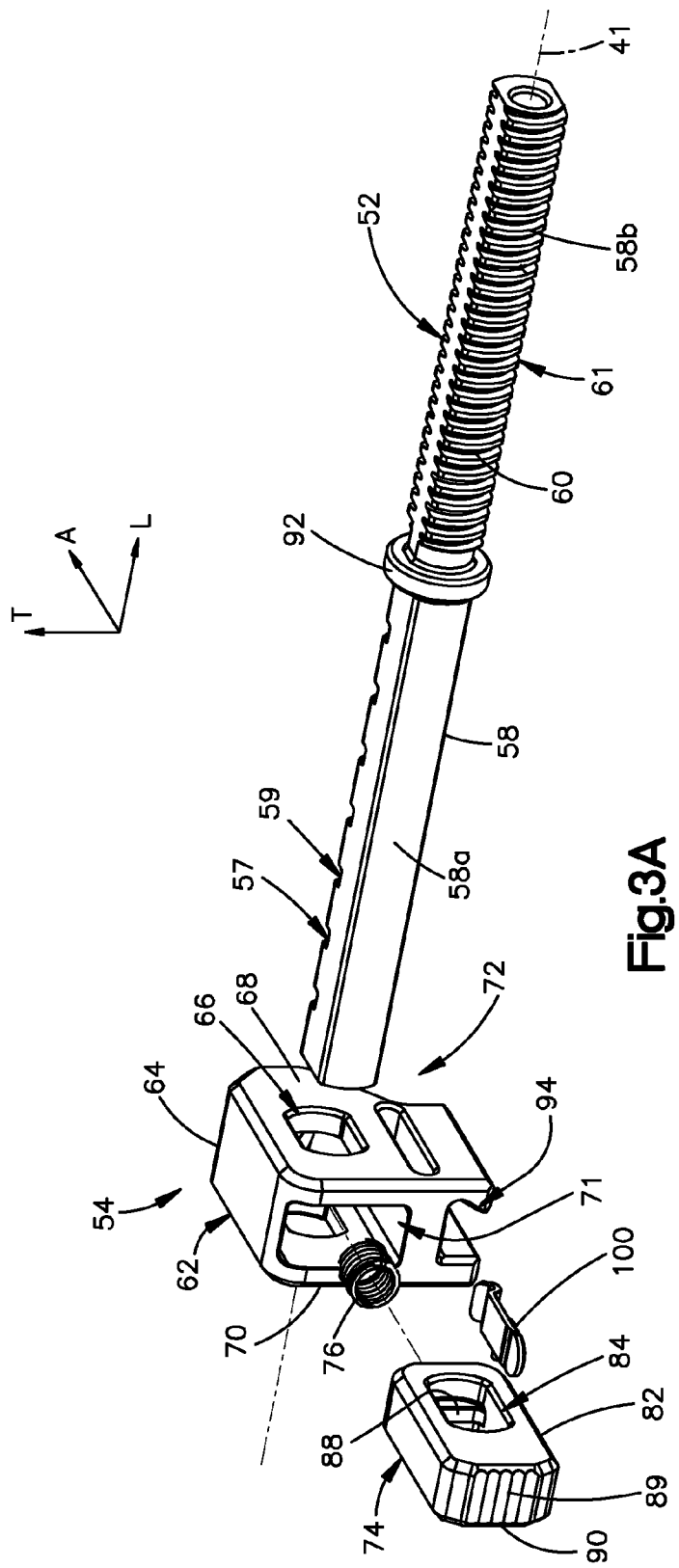
FIG. 3A is an exploded perspective view of a coarse adjustment assembly of the vertebral manipulation instrument illustrated in FIG. 2.

Referring also to FIG. 3A, the connecting rod 52 includes a rod body 58 is elongate along a central axis 41 that can extend along the longitudinal direction L. The rod body 58 can define a first or coarse adjustment portion 58a and a second or fine adjustment portion 58b that is spaced from the coarse adjustment portion 58a along the longitudinal direction L. For instance, the connecting rod 52 can define at least one first adjustment member, such as a plurality of first engagement members 59 that are carried by the rod body 58 and spaced from each other along the longitudinal direction L at first discrete increments along the longitudinal direction L. It should be appreciated that the first engagement members 59 define a first plurality of adjustment locations that are spaced from each other along the longitudinal direction L and the first discrete increments. For instance, the discrete increments can be substantially equal to each other or variable along the length of the coarse adjustment portion 58a.

Adjacent ones of the first engagement members 59, and thus the first adjustment locations, can be spaced from each other at any constant or variable first distance as desired, for instance between approximately 5 mm and approximately 15 mm, such as approximately 10 mm. The engagement members 59 can be configured as notches 57 that extend into the rod body 58, or can alternatively be configured as protrusions that extend out from the rod body 58 so as to define recesses between the protrusions, as desired. The fine adjustment portion 58b can define at least one second adjustment member, such as threads 60 that define a threaded region 61. The threads 60 can, for instance, be external threads and can define helical threads that are inclined along the longitudinal direction L. It should be appreciated that the threads 60, and thus the connecting rod 52, can define a continuous adjustment member that defines a second plurality of adjustment locations that can be spaced from each other at a second distance along the longitudinal direction L that is less than the first distance.

Referring now to FIG. 2 and FIGS. 3A-3B, the coarse adjustment assembly 54 includes a first carriage 62 that is configured to support the first arm 46 and includes a first carriage body 64 and an aperture 66 that extends through the first carriage body 64 along the longitudinal direction L. For instance, the first carriage body 64 can include first and second side walls 68 and 70 that are spaced from each other along the longitudinal direction L so as to define a void 71 that is disposed between the first and second side walls. The first carriage body 64 can further include an end wall 73 that is connected between the first and second side walls 68 and 70 and defines a rear end of the first carriage 62. The carriage can define an open front end that is opposite the rear end along the lateral direction A, such that the void 71 is disposed between the rear end and the front end along the lateral direction A. The aperture 66 can extend through each of the side walls 68 and 70, and can be sized slightly greater than the connecting rod 52, and can be shaped so as to correspond with the shape of the rod body 58, for instance at the coarse adjustment portion 58a. Accordingly, the aperture 66 is configured to receive the rod body 58 such that the rod body 58 is rotatably fixed with respect to the first carriage 62, and the rod body 58 is translatable through the aperture 66 in the first carriage 62 along the longitudinal direction L. Otherwise stated, the first carriage 62 is translatable along the rod body 58, for instance at the coarse adjustment portion 58a, along the longitudinal direction L.

The coarse adjustment assembly 54 can further include a locking assembly 72 that is configured to removably secure the first carriage 62 to the coarse adjustment portion 58a of the rod body 58 at the first engagement members 59. The locking assembly 72 can include a latch 74 and a biasing member, such as a spring member 76, which can be a coil spring, that is disposed between the first carriage body 64 and the latch 74, and is configured to bias the latch 74 into engagement with the connecting rod 52. For instance, the spring member 76 can extend between, and can bear against, the first carriage body 64, such as the end wall 73, and the latch 74. In accordance with the illustrated embodiment, the end wall 73 can define a seat 78 that can be recessed and is sized to receive a first end of the spring member 76, and the latch 74 can define a seat 80 that can be recessed and sized to receive a second end of the spring member 76 that is opposite the first and of the spring member 76. Thus, the spring member 76 can be captured between the first carriage body 64, for instance the end wall 73 of the first carriage body 64, and the latch 74. The spring member 76 can be a compression spring, or any alternatively constructed spring. During operation, the spring member 76 provides a force that biases the latch 74 toward the front end of the first carriage body 64, which as will now be described biases the latch 74 into engagement with the connecting rod 52. It should be appreciated, of course, that the spring member 76 can be alternatively constructed as desired, and can alternatively be disposed between the latch 74 and the first carriage 62 in any manner as desired so as to bias the latch 74 toward, and into engagement with, the connecting rod 52.

The latch 74 defines a latch body 82 and an aperture 84 that extends through the latch body 82 along the longitudinal direction L. The aperture 84 can be sized slightly greater than the connecting rod 52, and can be shaped so as to correspond with the shape of the rod body 58, for instance at the coarse adjustment portion 58a. Accordingly, the aperture 84 is configured to receive the rod body 58 such that the rod body 58 is rotatably fixed with respect to the latch 74, and the rod body 58 is translatable through the aperture 84 in the latch 74 along the longitudinal direction L. Otherwise stated, the latch 74 is translatable along the rod body 58, for instance at the coarse adjustment portion 58a, along the longitudinal direction L. The aperture 84 can, for instance, be sized substantially equal to the aperture 66 of the first carriage 62. The latch 74 can carry an engagement member 86 that is configured to selectively mate, for instance interlock, with at least one of the engagement members 59 of the connecting rod 52 so as to removably secure the first carriage 62 to the connecting rod 52 with respect to translation along the connecting rod 52 in the longitudinal direction L. For instance, the engagement member 86 can be defined by a wall 88 of the latch body 82, which can be an interior wall that at least partially defines the aperture 84.

The latch body 82 can be sized to be received in the void 71 of the first carriage body 64 such that the aperture 84 is substantially aligned with the aperture 66 so that the connecting rod 52 can be inserted through the apertures 66 and 84. When the connecting rod 52 is received by the apertures 66 and 84, the latch 74 is positioned in the void 71 such that the spring member 76 biases the engagement member 86 toward the rod body 58. The wall 88 of the latch 74 is sized so as to be selectively received in the notches 57 so as to secure the first carriage 62 to the connecting rod 52, for instance at the coarse adjustment portion 58a. The latch 74 defines an engagement surface 89, or button, which can be disposed at a front end 90 of the latch body 82 and can be disposed proximate to the open front end of the first carriage body 64. Thus, the front end 90 can receive a force that biases the latch 74 against the force of the spring member 76 and urges the engagement member 86 away from the connecting rod 52. When the force is removed, the spring member 76 can once again urge the engagement member 86 toward the connecting rod 52.

Thus, referring to FIG. 3C, during operation of the coarse adjustment assembly 54, the locking assembly 72, and thus the coarse adjustment assembly 54, can be in a locked configuration whereby the coarse adjustment assembly 54 is releasably locked to the connecting rod at one or more of the adjustment locations. For instance, the latch body 82 can be received in at least a select one of the notches 57 and the spring member 76 can provide a biasing force against the latch 74 that resists movement of the latch body 82 out of the select one of the notches 57. When the latch body 82 is disposed in the select one of the notches 57, the carriage 62 is translatably fixed to the connecting rod 52. Referring to FIG. 3D, a biasing force, for instance a user-applied biasing force, can act on the latch 74 against the force of the spring member 76 so as to iterate the locking assembly 72, and thus the coarse adjustment assembly 54, from the locked configuration to an unlocked configuration that allows the carriage 62 to travel along the connecting rod 52. In accordance with the illustrated embodiment, the biasing force can be applied to the latch 74, for instance at the engagement surface 89, that depresses the latch 74 into the void 71, thereby removing the latch body 82, and in particular the wall 88, from the select one of the notches 57. Once the latch body 82 has been removed from the select one of the notches, the first carriage 62 is translatable along the connecting rod 52 in the longitudinal direction L, both in a first direction toward the fine adjustment portion 58b, and thus the fine adjustment assembly 56 and the second arm 48, and in a second direction away from the fine adjustment portion 58b, and thus the fine adjustment assembly 56 and the second arm 48. Because the carriage 62 supports the first arm 46, the first arm 46 is thus also movable toward and away from the second arm 48. The biasing force can be released so as to allow the spring member 76 to bias the latch body 82 into another one of the notches 57 that is spaced from the select one of the notches along the longitudinal direction L either toward or away from the fine adjustment portion 58b, and thus the second arm 48, thereby locking the first arm 46 with respect to movement relative to the connecting rod 52 along the longitudinal direction L.

The connecting rod 52 can define at least one stop member 92 that can be configured as a protrusion that extends out from the rod body 58 so as to be dimensioned greater than the aperture 66. The stop member 92 can be disposed between the coarse adjustment portion 58a and the fine adjustment portion 58b of the rod body 58. The first carriage 62 is configured to abut the stop member 92 so as to prevent the first carriage 62 from translating from the coarse adjustment portion 58a to the fine adjustment portion 58b of the rod body 58. It should be appreciated that while the engagement members 59 of the connecting rod 52 can be configured as notches 57, and the engagement member 86 of the latch 74 is configured to be received in the notches 57, the engagement member 86 of the latch 74 can alternatively be configured as a notch and the engagement members 59 of the connecting rod 52 can be configured as protrusions that project out from the rod body 58 and are configured to be received in the engagement member 86 of the latch 74.

Referring again to FIGS. 2-3B, and as described above, the first carriage 62 is configured to support the first arm 46, such that the first arm 46 is movable with the first carriage 62 toward and away from the fine adjustment portion 58b, and thus the second arm 48. For instance, in accordance with one embodiment, the carriage 62 can define a channel 94 that extends into the first carriage body 64. The first arm 46 can define a first or distal end 47 and a second end 96 that is spaced from the distal end 47 along the transverse direction T. For instance, the second end 96 can define a proximal end of the first arm 46. The second end 96 can carry an insertion body 98 that is configured to be inserted into the channel 94 so as to couple the first arm 46 to the carriage. The channel 94 and the body 98 can define a dovetail joint so as to prevent removal of the insertion body 98 from the channel 94 along a direction perpendicular to the direction along which the insertion body 98 is inserted into the channel 94. It should be appreciated that any suitable alternatively constructed joint, such as a standard square or hex coupling could be used.

The coarse adjustment assembly 54 can further include a retention spring 100, which can be configured as a leaf spring, that is sized to fit into the channel 94 between the first carriage body 64 and the insertion body 98 when the insertion body 98 is disposed in the channel 94. The retention spring 100 is configured to bias the insertion body 98 against the first carriage body 64 so as to assist in retaining the insertion body 98 in the channel 94. The insertion body 98 can further interlock with the retention spring 100 as desired. For instance, the insertion body 98 can define a recess or a protrusion that receives or is received by a complementary protrusion or recess of the retention spring 100. Accordingly, movement of the first carriage 62 in a first longitudinal direction with respect to the connecting rod 52 causes the first arm 46 to move toward the second arm 48, and movement of the first carriage 62 in a second longitudinal direction with respect to the connecting rod 52 causes the first arm 46 to move away from the second arm 48. It should be appreciated, of course, that the first arm 46 can be supported by the first carriage 62 in any alternative manner as desired. For instance, the first arm 46 can be integral and monolithic with the carriage 62, or removably attached to the carriage 62 in any alternative manner as desired. For instance, the first arm 46 can be hingedly attached to the first carriage 62, and thus hingedly supported by the connecting rod 52. In accordance with one embodiment, the first arm 48 can pivot with respect to the first carriage 62, and thus with respect to the connecting rod 52, about an axis that extends along the longitudinal direction, the lateral direction, or any suitable alternative direction.

Referring now to FIGS. 2, 4, and 5A-5D, the fine adjustment assembly 56 includes a traveler assembly 102 that is configured to ride along the fine adjustment portion 58b of the rod body 58, an actuation assembly 104 that is configured to actuate the traveler assembly 102 to translate along the fine adjustment portion 58b, and a second carriage 106 that is supported by the traveler assembly 102 and translated along with the traveler assembly 102 with respect to the fine adjustment portion 58b. The second carriage 106 can further support the second arm 48 such that the second arm 48 translates along with the second carriage 106 with respect to the fine adjustment portion 58b. The fine adjustment portion 58b can define the threads 60 that are inclined along the longitudinal direction L. The fine adjustment portion 58b can be generally cylindrical with one or more unthreaded surfaces 108 that interrupt the threads 60. For instance, the fine adjustment portion 58b can define two opposed unthreaded surfaces 108 that geometrically differ from the cylindrical threads 60. For instance, the unthreaded surfaces 108 can define flats 110 that divide the threads 60 into first and second thread portions 60a and 60b. The first and second thread portions 60a and 60b can be continuous with each other, that is they would be continuous with each other if continued along the unthreaded surfaces 108.

The traveler assembly 102 can include a traveler member 112 having a traveler body 114 that carries threads 118 configured to mate with the threads 60 of the fine adjustment portion 58b of the rod body 58. For instance, the traveler member 112 can define an aperture 116 that extends through the traveler body 114 along the longitudinal direction L. The threads 118 can be internal threads that surround the aperture 116. The aperture 116 can be a cylindrical aperture, elongate along the longitudinal direction L and dimensioned to receive the fine adjustment portion 58b such that internal threads 118 mate with the external threads 60 of the fine adjustment portion 58b. Accordingly, as the traveler member 112 rotates with respect to the connecting rod 52 about the central axis 41 of the connecting rod 52 in a first rotational direction, the traveler member body 114 moves toward the coarse adjustment portion 58a, and thus the coarse adjustment assembly 54, including the first arm 46. As the traveler member 112 rotates with respect to the connecting rod 52 about the central axis 41 of the connecting rod 52 in a second rotational direction that is opposite the first rotational direction, the traveler body 114 moves away from the coarse adjustment portion 58a, and thus the coarse adjustment assembly 54, including the first arm 46.

The traveler assembly 102 can further include at least one guide member, such as first and second guide members 120a and 120b that are attached to the second carriage 106 such that the traveler member 112 is captured between the first and second guide members 120a and 120b. For instance, the traveler assembly 102 can include at least one washer 121 that is disposed between the traveler member 112 and one of the first and second guide members 120a and 120b. For instance, in accordance with the illustrated embodiment, the washer 121 is disposed between the second guide member 120b and the traveler member 112. Thus, it can also be said that the washer 121 is disposed between a second carriage body 126 of the second carriage 106, for instance a side wall 130 of the second carriage 106, and the traveler member 112. Alternatively, the washer 121 can be disposed between the first guide member 120a and the traveler member 112. Alternatively still, one or more washers 121 can be disposed between the first guide member 120a and the traveler member 112, and one or more washers 121 can be disposed between the second guide member 120b and the traveler member 112. The washer 121 can assist in locating the traveler member 112 such that gear teeth 150 of the first traveler member 112 are in a desired location with respect to the longitudinal direction L so as to interdigitate with complementary gear teeth 176 of a drive gear 174, as is described in more detail below.

The first and second guide members 120a and 120b are further configured to be coupled to the rod body 58 at the fine adjustment portion 58b so as to be rotatably fixed to the rod body 58 at the fine adjustment portion 58b, but rotatable with respect to the traveler member 112. Alternatively, or additionally, the first and second guide members 120a and 120b can be attached to the traveler member 112. Thus, as the traveler member 112 rotates with respect to the rod body 58, the guide members 120a and 120b travel along the rod body 58 but do not rotate with respect to the rod body 58. Thus, the guide members 120a and 120b are rotatably coupled to the traveler member 112 so as to rotate relative to the traveler member about the central axis 41. For instance, the first and second guide members 120a and 120b can include respective first and second guide bodies 122a and 122b and respective first and second apertures 124a and 124b that extend through the guide bodies 122a and 122b along the longitudinal direction L.

The apertures 124a and 124b can be sized slightly greater than the connecting rod 52, and can be shaped so as to correspond with the shape of the rod body 58 at the fine adjustment portion 58b. For instance, the first and second guide bodies 122a and 122b can define flat interior surfaces 125a and 125b, respectively, that at least partially define the apertures 124a and 124b and correspond in shape with the flat regions 110 of the fine adjustment portion 58b. Accordingly, the apertures 124a and 124b are configured to receive the rod body 58 such that the rod body 58 is rotatably fixed with respect to each of the first and second guide members 120a and 120b. Internal surfaces of the guide bodies 122a and 122b that define the apertures 124a and 124b can be unthreaded and substantially smooth and sized to translate along the unthreaded surfaces 108 of the fine adjustment portion 58b without causing the guide bodies 122a and 122b to impinge on the first and second thread portions 60a and 60b in a manner that could damage the first and second thread portions 60a and 60b. For instance, the internal surfaces of the guide bodies 122a and 122b can remain slightly spaced from the first and second thread portions 60a and 60b.

Each of the first and second guide members 120a and 120b are configured to attach to the second carriage 106 such that the guide members 120a and 120b are rotatable with respect to the traveler member 112. For instance, the guide members 120a and 120b can define respective flanges that are an aperture 127 that extends into or through a second carriage body 126 of the second carriage 106, so as to rotatably couple the guide members 120a and 120b to the second carriage 106. Alternatively, the guide members 120a and 120b can define respective recesses that receive corresponding flanges of the second carriage 106. In accordance with the illustrated embodiment, the first and second guide members 120a and 120b are configured to attach to opposed ends of the traveler member 112 that are spaced along the longitudinal direction L, such that traveler body 114 is disposed between the first and second guide members 120a and 120b. It should thus be appreciated that during operation, as the traveler 112 rotates with respect to the fine adjustment portion 58b of the rod body 58 so as to cause the traveler assembly 102 to translate along the rod body 58, the traveler 112 further rotates with respect to the guide members 120a and 120b, which remain rotatably fixed with respect to the fine adjustment portion 58b of the rod body 58.

Figure 4:
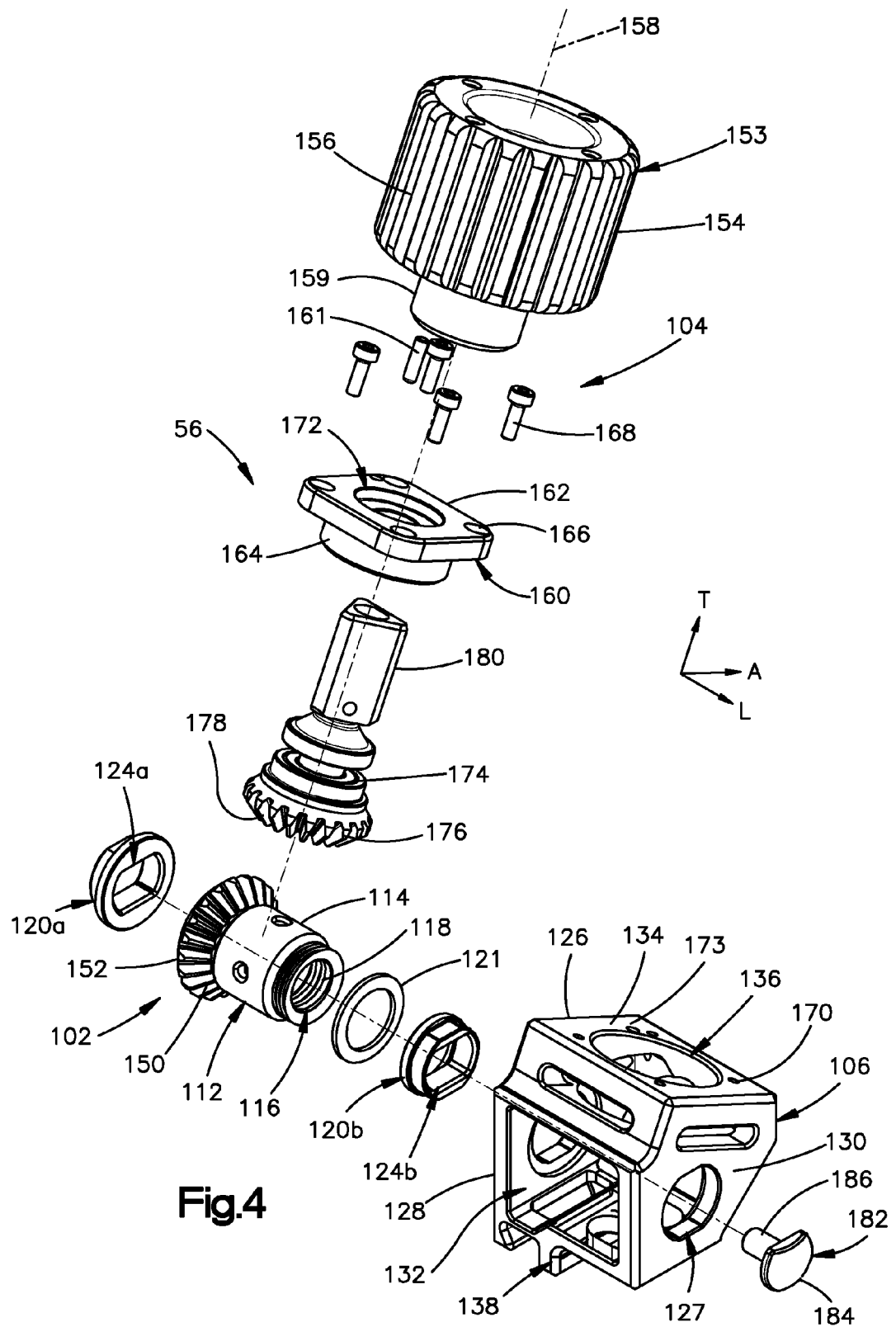
FIG. 4 is an exploded perspective view of a fine adjustment assembly of the vertebral manipulation instrument illustrated in FIG. 2.
Figure 5A:
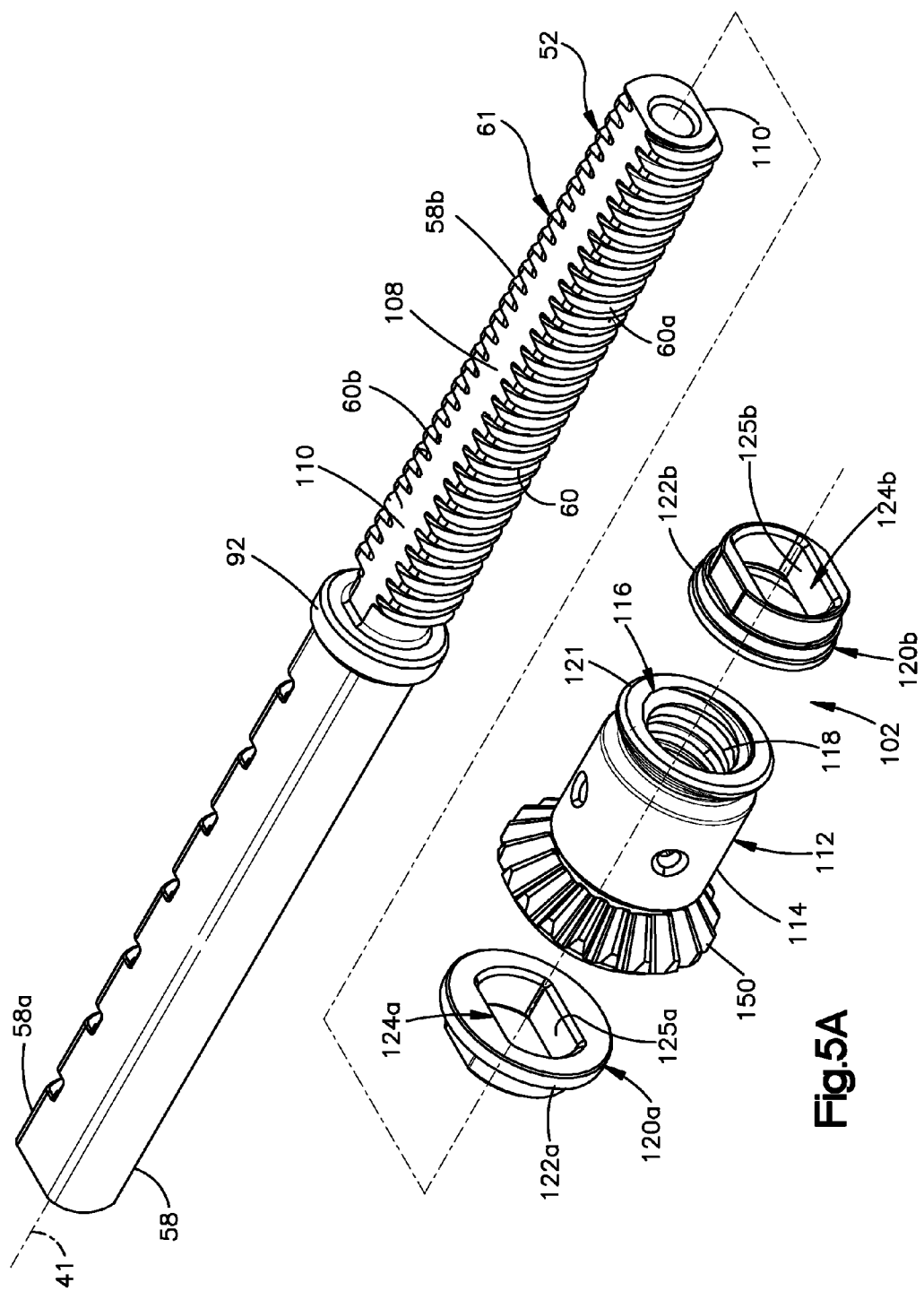
FIG. 5A is an exploded perspective view of a traveler assembly of the fine adjustment assembly illustrated in FIG. 4.
Figure 5D:
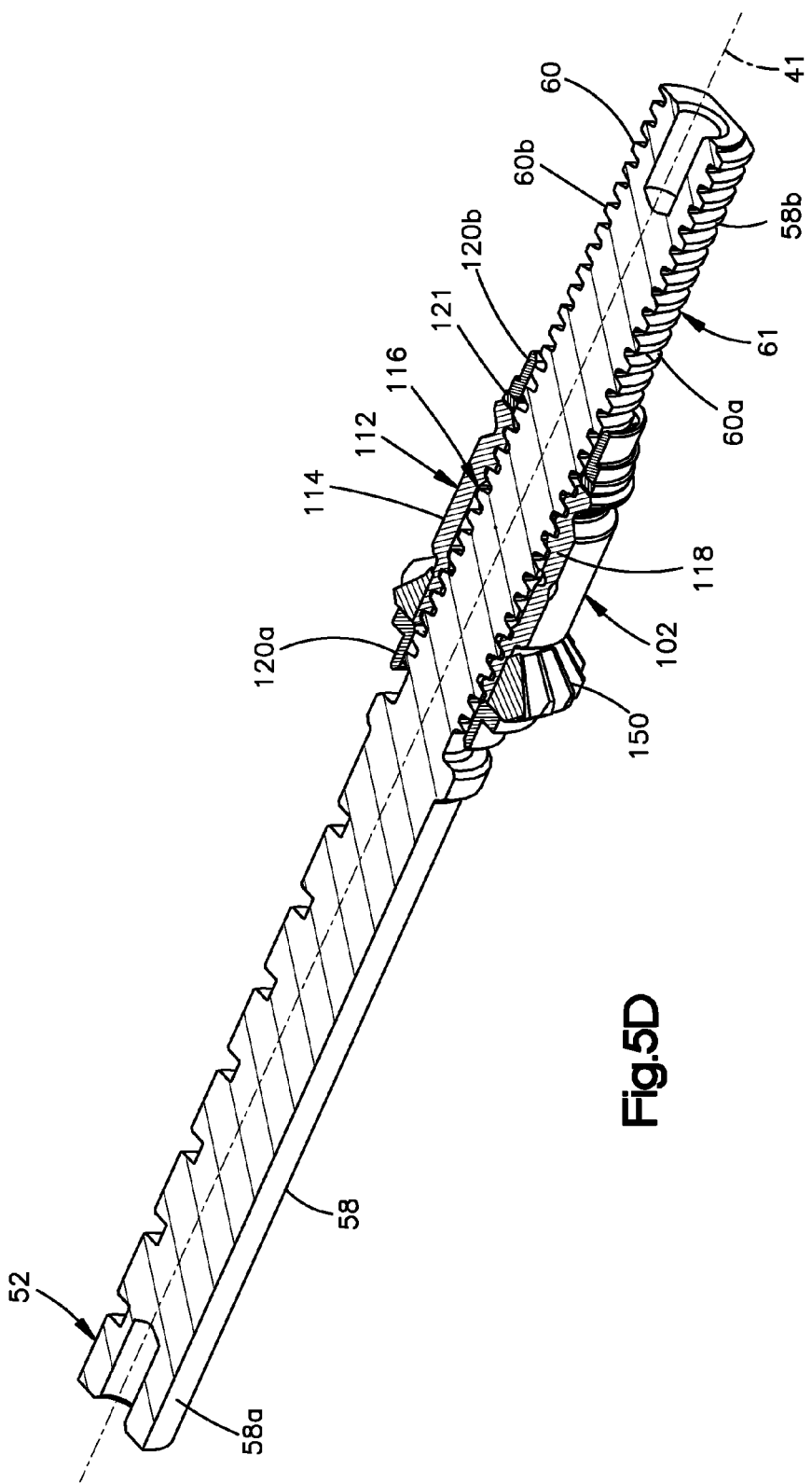
FIG. 5D is a sectional perspective view of the traveler assembly illustrated in FIG. 5A.

With continuing reference to FIGS. 2 and 4, the second carriage 106 is configured to support the second arm 48 and includes a second carriage body 126 and an aperture 127 that extends through the second carriage body 126 along the longitudinal direction L. For instance, the second carriage body 126 can include first and second side walls 128 and 130 that are spaced from each other along the longitudinal direction L so as to define a void 132 that is disposed between the first and second side walls 128 and 130. The second carriage body 126 can further include a support wall 134, which can be an upper wall, that is connected between the first and second side walls 128 and 130. The second carriage body 126 can define an aperture 136 that extends through the support wall 134 and is open to the void 132. The aperture 127 can extend through each of the first and second side walls 128 and 130, and can be sized slightly greater than the connecting rod 52, and can be shaped so as to correspond with the shape of the first and second guide member bodies 122a and 122b, respectively.

Accordingly, the first guide member body 122a is configured to attach to the first side wall 128 in the aperture 127 that extends through the first side wall 128 such that the first guide member 120a is rotatably fixed to the second carriage 106, and the second guide member body 122b is configured to attach to the second side wall 130 in the aperture 127 that extends through the second side wall 130 such that the second guide member 120b is rotatably fixed to the second carriage 106. Thus, the fine adjustment portion 128b of the rod body 128 is configured to extend through the first guide member 120a, the traveler member 112, the second guide member 120b, and the second carriage 106. The second carriage 106 and the first and second guide members 120a and 120b are configured to remain fixed to the fine adjustment portion 58b of the rod body 58 as the traveler member 112 rotates with respect to the fine adjustment portion 58b of the rod body 58. It should be appreciated that when the first and second guide members 120a and 120b are attached to the second carriage 106 such that the traveler member 112 is disposed between the first and second guide members 120a and 120b, the traveler member 112 is disposed in the void 132. It should be appreciated that the first and second guide members 120a and 120b can attach to the second carriage 106 in any suitable alternative manner as desired.

As described above, the second carriage 106 is configured to support the second arm 48, such that the second arm 48 is movable with the second carriage 106 toward and away from the coarse adjustment portion 58a, and thus the first arm 46. For instance, in accordance with one embodiment, the second carriage 106 can define a channel 138 that extends into the second carriage body 126. The second arm 48 can define a first or distal end 49 and a second end 140 that is spaced from the distal end 49 along the transverse direction T. For instance, the second end 140 can define a proximal end of the second arm 48. The second end 140 can carry an insertion body 142 that is configured to be inserted into the channel 138 so as to couple the second arm 48 to the second carriage 106. The channel 138 and the insertion body 142 can define a dovetail joint so as to prevent removal of the insertion body 142 from the channel 138 along a direction perpendicular to the direction along which the insertion body 142 is inserted into the channel 138. It should be appreciated that any suitable alternatively constructed joint, such as a standard square or hex coupling could be used.

The fine adjustment assembly 56 can further include a retention spring 144 that is sized to fit into the channel 138 between the second carriage body 126 and the insertion body 142 when the insertion body 142 is disposed in the channel 138. The retention spring 144 is configured to bias the insertion body 142 against the second carriage body 126 so as to assist in retaining the insertion body 142 in the channel 138. The insertion body 142 can further interlock with the retention spring 144 as desired. For instance, the insertion body 142 can define a recess or a protrusion that receives or is received by a complementary protrusion or recess of the retention spring 144. It should be appreciated, of course, that the second arm 48 can be supported by the second carriage 106 in any alternative manner as desired. For instance, the second arm 48 can be integral and monolithic with the carriage 106, or removably attached to the carriage 106 in any alternative manner as desired. For instance, the second arm 48 can be hingedly attached to the second carriage 106, and thus hingedly supported by the connecting rod 52. In accordance with one embodiment, the second arm 48 can pivot with respect to the second carriage 106, and thus with respect to the connecting rod, about an axis that extends along the longitudinal direction, the lateral direction, or any suitable alternative direction.

Accordingly, as the traveler member 112 rotates with respect to the connecting rod 52 about the central axis 41 of the connecting rod 52 in the first rotational direction, the second arm 48 moves toward the first arm 46. As the traveler member 112 rotates with respect to the connecting rod 52 about the central axis 41 of the connecting rod 52 in the second rotational direction the second arm 48 moves away from the first arm 46.

With further reference to FIGS. 2 and 4, the fine adjustment assembly 56 further includes the actuation assembly 104 that is configured to selectively rotate the traveler 112 in the first and second directions so as to cause the fine adjustment assembly 56 to translate toward and away from the coarse adjustment assembly 54, and thus the coarse adjustment portion 58a, respectively. For instance, the traveler member 112 can include a first plurality of gear teeth 150 that are supported by the traveler body 114. For instance the gear teeth 150 can define a bevel gear that is rotatable about the central axis 41 and whose gear teeth 150 define tooth bearing surfaces 152 that are inclined with respect to the central axis 41 when the traveler 112 is threadedly attached to the fine adjustment portion 58b. The gear teeth 150 can be monolithic with the traveler body 114, or otherwise attached to the traveler body 114 in any manner as desired.

The actuation assembly 104 is configured to be supported by the second carriage 106 so as to engage the traveler assembly 102 so as to selectively rotate the traveler member 112 in the first and second rotational directions. The actuation assembly 104 can include an actuator 153, such as a knob, having a grip member 154 that defines an outer grip surface 156 that can be knurled or otherwise ergonomically friendly. The actuator 153 is configured to rotate about a central axis 158, and includes a shaft 159 that extends away from the grip member 154, for instance along the central axis 158. The actuation assembly 104 can further include a support member 160 that can be configured to be attached to the second carriage 106, for instance to the support wall 134 of the second carriage body 126.

The support member 160 can include an attachment portion 162, which can be a flange, that is configured to attach to the support wall 134, and a support member 164, which can be a bushing, that extends from the attachment portion 162, through the aperture 136 of the second carriage 106, and toward the void 132 when the attachment portion 162, and thus the support member 160, is supported by the second carriage 106. For instance, the attachment portion 162, and thus the support member 160, can be attached to the support wall 134 or supported by the support member in accordance with any suitable embodiment. The support member 160 can, for example, define at least one aperture 166 such as a plurality of apertures 166 that extend through the attachment portion 162 and are sized to receive fixation members 168, such as screws, that are configured to be driven through the apertures 166 and into respective apertures 170 that extend into the second carriage body 126, such as the support wall 134, so as to attach the support member 160 to the second carriage 106. The support member 160 defines an aperture 172 that extends through the attachment portion 162 and the support member 164. The aperture 172 can be cylindrical, and can have a portion, for instance an upper portion, that is sized slightly greater than the shaft 159 of the actuator 153 such that the shaft 159 extends at least into the aperture 172. The shaft 159 can also be cylindrical such that the shaft 159 is configured to be inserted into the aperture 172, thereby causing the second carriage 106, and the support member 160, to support the actuator 153. The actuator 153 is configured to rotate with respect to the support member 160, and the second carriage 106, in the aperture 172. The actuation assembly 104 can further include a pin 161 that is configured to extend into a corresponding aperture 173 that extends into the second carriage body 126, for instance at the support wall 134. The pin 161 is configured to absorb shear forces during operation that could otherwise be transmitted to the fixation members 168.

The actuation assembly 104 can further include a drive gear 174 that is coupled to the actuator 153 and configured to drive the traveler 112 to rotate along the connecting rod 52. For instance, one or both of the shaft 159 and the support member 164 are configured to attach to the drive gear 174 that is configured to rotate about the central axis 158 that is angularly offset, for instance substantially perpendicular, with respect to the central axis 41. The drive gear 174 can be configured as a bevel gear that includes a second plurality of gear teeth 176 configured to mate with the first plurality of gear teeth 150 of the traveler member 112. For instance the gear teeth 176 can define a bevel gear that is rotatable about the central axis 158 whose gear teeth 176 define tooth bearing surfaces 178 that are inclined with respect to the central axis 158. Because rotation of the drive gear 174 causes the traveler member 112 to rotate, the traveler member 112 can be referred to as a driven gear. The drive gear 174 and the driven gear of the traveler member 112 can define a 1:1 ratio, though it should be appreciated that the gear ratio could be greater or less than 1:1, such that one revolution of the drive gear 174 can cause the traveler to rotate more than one revolution, less than one revolution, or one revolution about the connecting rod 52. It should be appreciated that the drive gear 174 and the driven gear of the traveler member 112 can be alternatively configured as desired. For instance, the drive gear 174 and the driven gear can alternatively be configured as spiral gears or any suitable alternatively constructed gears that intermesh such that rotation of the drive gear 174 causes the traveler 112 to rotate.

The drive gear 174 can further include a shaft 180 that is elongate along the central axis 158, and is configured to attach to the actuator 153 so as to be rotatably fixed to the actuator 153. Accordingly, rotation of the actuator 153 with respect to the second carriage 106 along the first rotational direction causes the drive gear 174 to rotate along the first rotational direction with respect to the second carriage 106. Similarly, rotation of the actuator 153 with respect to the second carriage 106 along the second rotational direction causes the drive gear 174 to rotate along the second rotational direction with respect to the second carriage 106. In accordance with the illustrated embodiment, the shaft can be non-cylindrical in cross section, such as triangular, and is configured to be received in a corresponding aperture that extends into the shaft 159 of the actuator 153 that is sized slightly greater than the shaft 180, and shaped so as to correspond to the shape of the shaft 180. Alternatively, the shaft 180 of the drive gear 174 can be attached to the actuator 153 in accordance with any suitable alternative embodiment.

When the shaft 180 of the drive gear 174 is rotatably fixed to the actuator 153, and the actuator 153 is supported by the second carriage 106, the gear teeth 176 of the drive gear 174 are configured to interdigitate with the gear teeth 150 of the traveler member 112. Thus, it can be said that the drive gear 174 is configured to be supported by the second carriage such that the gear teeth 176 interdigitate with the gear teeth 150 of the traveler member 112. Accordingly, when a torsional force is applied to the actuator 153 in the first rotational direction about the central axis 158, the drive gear 174 rotates in the first rotational direction about the central axis 158, thereby causing the gear teeth 176 of the drive gear to urge the gear teeth 150 of the traveler member 112 to rotate in the first rotational direction about the central axis 41, thereby threadedly driving the fine adjustment assembly 56 along the connecting rod 52 in the longitudinal direction L toward the coarse adjustment assembly 54. The stop member 92 is configured to abut the fine adjustment assembly 56 so as to prevent the fine adjustment assembly 56 from translating to the coarse adjustment portion 58a of the connecting rod 52. When a torsional force is applied to the actuator 153 in the second rotational direction about the central axis 158, the drive gear 174 rotates in the second rotational direction about the central axis 158, thereby urging the gear teeth 176 of the drive gear to cause the gear teeth 150 of the traveler member 112 to rotate in the second rotational direction about the central axis 41, thereby threadedly driving the fine adjustment assembly 56 along the connecting rod 52 in the longitudinal direction L away the coarse adjustment assembly 54.

The fine adjustment assembly 56 can further include an end cap 182 that includes a stop surface 184 and an attachment member 186 that extends out from the stop surface 184, and is configured to attach to the connecting rod 52, for instance along the central axis 41. In accordance with one embodiment, the attachment member 186 is configured to be received in the rod body 58, for instance in an end of the rod body 58. The stop surface 184 can be sized so as to abut one or more of the first and second side walls 128 and 130, the first guide member 120a, the second guide member 120b, and the traveler member 112 so as to prevent the connecting rod 52 from disengaging the fine adjustment assembly 54.

As described above, the fine adjustment assembly 56 can threadedly engage the threads 60 of the fine adjustment portion 58b so as to cause the fine adjustment assembly 56 to travel along the connecting rod 52 in the longitudinal direction L. It should be appreciated that the threads 60 can have a single lead or multiple leads to facilitate attachment of the fine adjustment assembly to the connecting rod 52. Thus, movement of the threads 118 of the traveler member 112 along the threads 60 can be between a first adjustment location of the threads 60, and thus the connecting rod 52, to a second adjustment location of the threads 60, and thus the connecting rod 52. The second adjustment location of the threads 60 is spaced from the coarse adjustment assembly 54 a distance that is different than the distance from which the first adjustment location of the threads 60 is spaced from the coarse adjustment assembly 54. Accordingly, the fine adjustment assembly 56 is configured to translate with respect to the connecting rod 52 toward and away from, respectively, the coarse adjustment assembly 54 along the longitudinal direction L between the first and second adjustment locations of the second plurality of adjustment locations of the connecting rod 52. The first and second adjustment locations of the threads 60 can be spaced from each other a second distance along the longitudinal direction L that is less than the first distance along which adjacent ones of the attachment locations of the coarse adjustment assembly 54 are spaced from each other. Thus, the fine adjustment assembly 56 provides for more incremental adjustment of the position of the one or both of the first and second arms 46 and 48 between first and second positions relative to the other of the first and second arms 46 and 48, compared to the incremental adjustment of the coarse adjustment assembly 54. The fine adjustment assembly 56 is further configured to secure the first and second arms 46 and 48 in the first and second positions, as is described in more detail below.

While the fine adjustment assembly 56 has been described as threadedly attached to the connecting rod 52, it should be appreciated that the fine adjustment assembly 56 can alternatively be constructed as desired. For instance, the fine adjustment assembly 56 can be constructed as described above with respect to the coarse adjustment assembly 54, with the exception that adjacent ones of the adjustment locations are spaced closer together than the adjacent ones of the adjustment locations of the coarse adjustment assembly 54.

Referring again to FIGS. 1A-B, during operation of the vertebral manipulation instrument 44, the coarse adjustment assembly 54 can be actuated in the manner described herein so as to bring the first and second arms 46 and 48 in general alignment with the first and second vertebral bone anchors 28 and 30 so as to be positioned to distract and/or contract at least one or both of the first and second vertebral bone anchors 28 and 30 with respect to the other of the first and second vertebral bone anchors 28 and 30. For instance, the coarse adjustment assembly 54 unlocked in the manner described herein, and the first arm 46 can be translated along the connecting rod with respect to the second arm 48 so as to bring one or both of the first and second arms 46 and 48 closer to the other, or so as to bring one or both of the first and second arms 46 and 48 away from the other. The coarse adjustment assembly 54 can then be secured against the connecting rod 52 with respect to translation along the connecting rod 52 in the manner described herein so as to prevent further translation of the first arm 46 with respect to the connecting rod 52.

It is appreciated that the first and second arms 46 and 48 might be slightly misaligned with respect to the first and second vertebral bone anchors 28 and 30, respectively, after actuation of the coarse adjustment assembly 54. Accordingly, the fine adjustment assembly 56 can be actuated in the manner described herein so as to bring the first and second arms 46 and 48 into a desired aligned position with the first and second vertebral bone anchors 28 and 30, such that the first and second arms 46 and 48 are positioned to engage the first and second vertebral bone anchors 28 and 30. Accordingly, when the first and second arms 46 and 48 are engaged with the first and second vertebral bone anchors 28 and 30 that are attached to the first and second vertebrae 24 and 26, respectively, further movement of one or both of the first and second arms 46 and 48 away from the other causes the corresponding one or both of the first and second vertebral bone anchors 28 and 30 to move away from the other, thereby distracting one or both of the first and second vertebra 24 and 26 away from the other. Similarly, when the first and second arms 46 and 48 are engaged with the first and second vertebral bone anchors 28 and 30 that are attached to the first and second vertebrae 24 and 26, respectively, further movement of one or both of the first and second arms 46 and 48 toward the other causes the corresponding one or both of the first and second vertebral bone anchors 28 and 30 to move toward from the other, thereby compressing one or both of the first and second vertebra 24 and 26 toward the other. The fine adjustment assembly 56 allows for adjustment of the distance between the first and second arms 46 and 48 in finer increments than does the coarse adjustment assembly 54.

The fine adjustment assembly 56 can further secure the second carriage 106, and thus the second arm 48 and the second vertebral bone anchor 30, with respect to movement along the connecting rod 52 along the longitudinal direction L in the finer increments. It is appreciated that when the first and second vertebrae 24 and 26 are moved with respect to their anatomically normal position, the first and second vertebrae can apply vertebral forces to the vertebral manipulation instrument 44 that biases the first and second arms 46 and 48 to move toward the anatomically normal position. For instance, when the arms 46 and 48 apply a distraction force that separates the first and second vertebrae 24 and 26 from each other, the first and second vertebrae 24 and 26 can apply a vertebral compression force that biases the first and second arms 46 and 48 to move along the connecting rod 52 toward each other along the longitudinal direction L. Conversely, when the arms 46 and 48 apply a compression force that brings the first and second vertebrae 24 and 26 closer to each other, the first and second vertebrae 24 and 26 can apply a vertebral distraction force that biases the first and second arms 46 and 48 to move along the connecting rod 52 away from each other along the longitudinal direction L. The coarse adjustment assembly 54 illustrated in FIG. 30 is configured to secure the first carriage, and thus the first arm 46, with respect to movement along the connecting rod 52 along the longitudinal direction L in the manner described above.

The fine adjustment assembly 56 is likewise configured to secure the second carriage 106, and thus the second arm 48, from moving along the connecting rod 52 along the longitudinal direction L, for instance in response to the vertebral forces. In accordance with one embodiment, the threads 118 of the traveler member 112 can define a lead angle with respect to the longitudinal direction L that is sufficient such that a substantial portion of the vertebral forces that would tend to bias the traveler member 112 to move along the connecting rod 52 in the longitudinal direction L are absorbed by static friction between the threads 118 of the traveler 112 and the threads 60 of the connecting rod 52 before the vertebral forces are communicated to the gear teeth 150. In one embodiment, all longitudinal vertebral forces can be absorbed at the interface between the threads 118 of the traveler member 112 and the threads 60 of the connecting rod 52. Thus, the vertebral forces are insufficient to cause the traveler member 112 to inadvertently travel along the connecting rod 52 during operation. It should be appreciated that the fine adjustment assembly 56 can further be constructed so that any vertebral forces that do travel past the interface between the threads 118 of the traveler 112 and the threads 60 of the connecting rod 52 to the gear teeth 150 can be are absorbed at the interface between the gear teeth 150 of the traveler member 112 and the gear teeth 176 of the drive gear 174.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one embodiment may be used and/or interchanged with features described in another embodiment. The presently disclosed embodiments are therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art.

What is claimed:

1. A vertebral manipulation instrument comprising:
   a connecting rod that is elongate along a longitudinal direction, the connecting rod defining a first plurality of adjustment locations and a second plurality of adjustment locations;
   a first arm supported by the connecting rod and oriented substantially transverse to the connecting rod, the first arm configured to engage a first bone fixation member;
   a second arm supported by the connecting rod and oriented substantially transverse to the connecting rod, the second arm configured to engage a second bone fixation member,
   a coarse adjustment assembly that is configured to be actuated so as to move the first arm from a first one of the first plurality of adjustment locations to a second one of the first plurality of adjustment locations that is disposed adjacent the first one of the first plurality of adjustment locations, and lock the first arm with respect to movement from the second one of the first plurality of adjustment locations, the first one of the first plurality of adjustment locations spaced a first distance from the second one of the adjustment locations along the longitudinal direction; and
   a fine adjustment assembly that is configured to be actuated so as to move the second arm from a first one of the second plurality of adjustment locations to a second one of the second plurality of adjustment locations that is spaced a second distance from the first one of the second plurality of adjustment locations a second distance along the longitudinal direction, the second distance less than the first distance.

2. The vertebral manipulation instrument as recited in claim 1, wherein the connecting rod defines a coarse adjustment portion that carries the first plurality of adjustment locations spaced the first distance from each other along the longitudinal direction, and the connecting rod further defines a fine adjustment portion that carries the second plurality of adjustment locations that are spaced from each other along the longitudinal direction the second distance that is less than the first distance.

3. The vertebral manipulation instrument as recited in claim 2, wherein the course adjustment assembly couples the first arm to the coarse adjustment portion, and the fine adjustment assembly couples the second arm to the fine adjustment portion.

4. The vertebral manipulation instrument as recited in claim 3, wherein the connecting rod carries a plurality of engagement members that define the first plurality of adjustment locations, and the coarse adjustment assembly includes a carriage that supports the first arm relative to the connecting rod, the carriage supporting an engagement member that is configured to selectively mate with the engagement members of the connecting rod so as to lock the carriage with respect to movement relative to the connecting rod along the longitudinal direction.

5. The vertebral manipulation instrument as recited in claim 4, wherein the connecting rod includes a connecting rod body, and the first plurality of adjustment locations comprise recesses that extend into the connecting rod body, and the engagement member of the course adjustment assembly is configured to be selectively received in the recesses.

6. The vertebral manipulation instrument as recited in claim 5, wherein the course adjustment assembly comprises a latch movably supported by the carriage, the latch defining the engagement member of the coarse adjustment assembly.

7. The vertebral manipulation instrument as recited in claim 6, wherein the latch is movable between an unlocked position whereby the carriage is slidable along the course adjustment portion in the longitudinal direction past at least one of the recesses, and a locked position whereby the latch is received in one of the recesses so as to prevent movement of the carriage along the course adjustment portion in the longitudinal direction.

8. The vertebral manipulation instrument as recited in claim 7, wherein the coarse adjustment assembly comprises a spring member that biases the latch toward the locked configuration.

9. The vertebral manipulation instrument as recited in claim 3, wherein the fine adjustment portion defines threads carried by the connecting rod, and the fine adjustment assembly comprises a traveler that threadedly engages the threads carried by the connecting rod, such that rotation of the traveler relative to the fine adjustment portion causes the second arm to move relative to the first arm along the longitudinal direction.

10. The vertebral manipulation instrument as recited in claim 9, wherein rotation of the traveler in a first direction relative to the fine adjustment portion brings the second arm closer to the first arm, and rotation of the traveler in a second direction opposite the first direction relative to the fine adjustment portion moves the second arm away from the first arm.

11. The vertebral manipulation instrument as recited in claim 9, further comprising at least one guide member that is attached to the traveler such that the guide member is rotatable with respect to the traveler and rotatably fixed with respect to the fine adjustment portion.

12. The vertebral manipulation instrument as recited in claim 9, further comprising a carriage that couples the second arm to the fine adjustment portion, the carriage attached to the guide member such that the carriage and the guide member are rotationally and translatably fixed to each other.

13. The vertebral manipulation instrument as recited in claim 12, wherein the traveler further comprises a plurality of gear teeth, and the fine adjustment assembly further comprises an actuation assembly that includes a plurality of gear teeth configured to drive the gear teeth of the traveler to selectively rotate relative to the fine adjustment portion.

14. The vertebral manipulation instrument as recited in claim 13, wherein the fine adjustment assembly comprises first and second guide members that are attached to first and second walls of the carriage so as to rotatably fix the connecting rod to the carriage, such that the gear teeth of the traveler and the gear teeth of the actuation assembly interdigitate in a void that is disposed between the first and second walls.

15. The vertebral manipulation instrument as recited in claim 13, wherein the gear teeth of the traveler define a bevel gear, and the gear teeth of the actuation assembly define a bevel gear.

16. A method for moving at least one of a first vertebra and a second vertebra with respect to the other of the first vertebra and the second vertebra, the method comprising the steps of:
attaching a first vertebral bone anchor to the first vertebra;
attaching a second vertebral bone anchor to the second vertebra;
engaging the first and second vertebral bone anchors with first and second arms, respectively, of a vertebral manipulation instrument, the engaging step including the steps of:
actuating a coarse adjustment assembly so as to cause the first arm to move along a connecting rod between first adjustment locations of the connecting rod, adjacent ones of the first adjustment locations spaced apart a first distance, and fixing the first arm to the connecting rod at one of the first adjustment locations; and
actuating a fine adjustment assembly so as to cause a traveler to threadedly rotate along the connecting rod so as to cause the traveler to translate along the connecting rod, thereby causing the second arm to move along the connecting rod between second adjustment locations of the connecting rod, wherein adjacent ones of the second adjustment locations are spaced apart a second distance that is less than the first distance; and
after the engaging step, actuating the fine adjustment assembly so as to cause the second arm to bias at least one of the first and second bone anchors to move with respect to the other of the first and second bone anchors.

17. The method as recited in claim 16, wherein the third actuating step comprises moving the second arm away from the first arm.

18. The method as recited in claim 16, wherein the third actuating step comprises moving the second arm toward from the first arm.

19. The method as recited in claim 16, further comprising the step of attaching a spinal fixation rod between the first and second vertebral bone anchors, and tightening the spinal fixation rod against one of the first and second bone anchors, such that the other of the first and second bone anchors is translatable along the spinal fixation rod.

20. The method as recited in claim 16, wherein the second actuating step further comprises applying a force to an actuator that supports a drive gear that is interdigitated with a driven gear of the traveler, so as to cause the driven gear to rotate with respect to the connecting rod.

21. The method as recited in claim 20, wherein the drive gear and the driven gear comprise bevel gears.

* * * * *